(12) United States Patent
Padgett et al.

(10) Patent No.: US 7,888,475 B2
(45) Date of Patent: Feb. 15, 2011

(54) INTERFERON ALPHA AND INTERFERON KAPPA FUSION PROTEIN

(76) Inventors: Hal S. Padgett, 638 Blossom Oak Ct., Vacaville, CA (US) 95688; Fakhrieh S. Vojdani, 1626 Cape Cod Ct., Davis, CA (US) 95616; Andrew A. Vaewhongs, 999 Marshall Rd., Apartment 40, Vacaville, CA (US) 95687

( * ) Notice: Subject to any disclaimer, the term of this patent is extended or adjusted under 35 U.S.C. 154(b) by 0 days.

(21) Appl. No.: 12/560,391

(22) Filed: Sep. 15, 2009

(65) Prior Publication Data

US 2010/0121030 A1    May 13, 2010

Related U.S. Application Data

(60) Provisional application No. 61/097,077, filed on Sep. 15, 2008.

(51) Int. Cl.
*C07K 17/00* (2006.01)
*C12N 15/00* (2006.01)
*C07H 21/04* (2006.01)

(52) U.S. Cl. .................. 530/351; 435/69.7; 536/23.4; 536/23.52

(58) Field of Classification Search .................. None
See application file for complete search history.

(56) References Cited

U.S. PATENT DOCUMENTS 7,056,740 B2 *    6/2006   Padgett et al. ............... 435/440

* cited by examiner

*Primary Examiner*—Christie J Saoud
*Assistant Examiner*—Jegatheesan Seharaseyon
(74) *Attorney, Agent, or Firm*—Wayne P. Fitzmaurice

(57) ABSTRACT

Herein is described a system to combat poxvirus infection wherein antagonists are developed that bind the soluble cytokine receptor but have no significant biological activity in the host, effectively blocking the virus-mediated suppressor of interferon function, thereby permitting the host's own cytokines to stimulate an antiviral response. Alternatively, interferon molecules can be developed that retain biological activity on their native receptors but fail to bind the viral cytokine binding protein, thereby circumventing this virus immune modulation mechanism.

2 Claims, 4 Drawing Sheets

SEQ ID NO: 1

ATGGGAAAAATGGCTTCTCTATTTGCCACATTTTTAGTGGTTTTAGTGTCACTTAGCTT
AGCTAGCGAAAGCTCCGCCTGCGACTTACCAGAAACTCACAGTCTTGATAATAGGAGAACTTTGATGTTA
TTGGCTCAGATGAGTAGAATATCTCCTTCTTCTTGTTTGATGGATAGACATGACTTCGGATTTCCACAAG
AGGAGTTTGATGGTAATCAATTTCAAAAGGCTCCAGCTATTTCTGTATTACATGAGTTGATTCAGCAAAT
TTTCAATCTGTTTACTACAAAGGATTCATCTGCTGCATGGGATGAGGATCTCTTAGATAAATTTTGTACT
GAATTGTATCAACAGCTTAATGATTTGGAAGCTTGTGTGATGCAGGAGGAGAGAGTGGGTGAGACTCCAT
TGATGAATGCTGACTCCATACTGGCAGTGAAGAAATACTTCAGACGTATCACACTTTACCTGACAGAAAA
GAAATACTCACCTTGTGCCTGGGAGGTTGTCAGAGCGGAAATACGAAGATGTTTGTATTATTTTTATAAG
TTTACTGCACTATTCCGTAGAAAAGAGCACCATCACCATCACCATAAGGACGAACTGTGA

>10442_H8

SEQ ID NO: 2

ATGGGAAAAATGGCTTCTCTATTTGCCACATTTTTAGTGGTTTTAGTGTCACTTAGCTT
AGCTAGCGAAAGCTCCGCCTGCGACTTACCAGAAACTCACAGTCTTGATAATAGGAGAACTTTGATGTTA
TTGGCTCAGATGAGTAGAATATCTCCTTCTTCTTGTTTGATGGATAGACATGACTTCGGATTTCCACAAG
AGGAGTTTGATGGTAATCAATTTCAAAAGGCTCCAGCTATTTCTGTATTACATGAGTTGATTCAGCAAAT
TTTCAATCTGTTTACTACAAAGGATTCATCTGCTGCATGGGATGAGGATCTCTTAGATAAATTTTGTACT
GAATTGTATCAACAGCTTAATGATTTGGAAGCTTGTGTGATGCAGGAGGAGAGAGTGGGTGAGACTCCAT
TGATGAATGCTGACTCCATACTGGCAGTGAAGAAATACTTCAGACGTATCACACTTTACCTGACAGAAAA
GAAATACTCACCTTGTGCCTGGGAGGTTGTCAGAGCGGAAATACGAAGATGTTTGTATTATTTTTATAAG
TTTACTGCACTATTACGTAGAAAAGAGCACCATCACCATCACCATAAGGACGAACTGTGA

>10453_H9

SEQ ID NO: 3

ATGGGAAAAATGGCTTCTCTATTTGCCACATTTTTAGTGGTTTTAGTGTCACTTAGCTT
AGCTAGCGAAAGCTCCGCCTGCGACTTACCAGAAACTCACAGTCTTGATAATAGGAGAACTTTGATGTTA
TTGGCTCAGATGAGTAGAATATCTCCTTCTTCTTGTTTGATGGATAGACATGACTTCGGATTTCCACAAG
AGGAGTTTGATGGTAATCAATTTCAAAAGGCTCCAGCTATTTCTGTATTACATGAGTTGATTCAGCAAAT
TTTCAATCTGTTTACTACAAAGGATTCATCTGCTGCATGGGATGAGGATCTCTTAGATAAATTTTGTACT
GAATTGTATCAACAGCTTAATGATTTGGAAGCTTGTGTGATGCAGGAGGAGAGAGTGGGTGAGACTCCAT
TGATGAATGCTGACTCCATACTGGCAGTGAAGAAATACTTCAGACGTATCACACTTTACCTGACAGAAAA
GAAATACTCACCTTGTGCCTGGGAGGTTGTCAGAGCGGAAATACGAAGATGTTTGTATTATTTTTATAAG
TTTACTGCACTATTCCGTAGAAAACACCATCACCATCACCATAAGGACGAACTGTGA

FIGURE 3

SEQ ID NO: 4

MGKMASLFATFLVVLVSLSLASESSACDLPETHSLDNRRTLMLLAQMSRISPSSCLMDRHDFGFPQEEFDGNQFQK
APAISVLHELIQQIFNLFTTKDSSAAWDEDLLDKFCTELYQQLNDLEACVMQEERVGETPLMNADSILAVKKYFRR
ITLYLTEKKYSPCAWEVVRAEIRRCLYYFYKFTALFRRKEHHHHHHKDEL

SEQ ID NO: 5

MGKMASLFATFLVVLVSLSLASESSACDLPETHSLDNRRTLMLLAQMSRISPSSCLMDRHDFGFPQEEFDGNQFQK
APAISVLHELIQQIFNLFTTKDSSAAWDEDLLDKFCTELYQQLNDLEACVMQEERVGETPLMNADSILAVKKYFRR
ITLYLTEKKYSPCAWEVVRAEIRRCLYYFYKFTALLRRKEHHHHHHKDEL

SEQ ID NO: 6

MGKMASLFATFLVVLVSLSLASESSACDLPETHSLDNRRTLMLLAQMSRISPSSCLMDRHDFGFPQEEFDGNQFQK
APAISVLHELIQQIFNLFTTKDSSAAWDEDLLDKFCTELYQQLNDLEACVMQEERVGETPLMNADSILAVKKYFRR
ITLYLTEKKYSPCAWEVVRAEIRRCLYYFYKFTALFRRKHHHHHHKDEL

SEQ ID NO: 7

MGKMASLFATFLVVLVSLSLASESSACDLPETHSLDNRRTLMLLAQMSRISPSSCLMDRHDFGFPQEEFDGNQFQK
APAISVLHELIQQIFNLFTTKDSSAAWDEDLLDKFCTELYQQLNDLEACVMQEERVGETPLMNADSILAVKKYFRR
ITLYLTEKKYSPCAWEVVRAEIRRCLYYFYKFTALFRRKE

SEQ ID NO: 8

MGKMASLFATFLVVLVSLSLASESSACDLPETHSLDNRRTLMLLAQMSRISPSSCLMDRHDFGFPQEEFDGNQFQK
APAISVLHELIQQIFNLFTTKDSSAAWDEDLLDKFCTELYQQLNDLEACVMQEERVGETPLMNADSILAVKKYFRR
ITLYLTEKKYSPCAWEVVRAEIRRCLYYFYKFTALLRRKE

SEQ ID NO: 9

MGKMASLFATFLVVLVSLSLASESSACDLPETHSLDNRRTLMLLAQMSRISPSSCLMDRHDFGFPQEEFDGNQFQK
APAISVLHELIQQIFNLFTTKDSSAAWDEDLLDKFCTELYQQLNDLEACVMQEERVGETPLMNADSILAVKKYFRR
ITLYLTEKKYSPCAWEVVRAEIRRCLYYFYKFTALFRRK

FIGURE 4

SEQUENCE LISTING

<160> NUMBER OF SEQ ID NOS: 9

<210> SEQ ID NO 1
<211> LENGTH: 609
<212> TYPE: DNA
<213> ORGANISM: Artificial
<220> FEATURE:
<223> OTHER INFORMATION: shuffled variant of human interferon

<400> SEQUENCE: 1

```
atgggaaaaa tggcttctct atttgccaca ttttagtgg ttttagtgtc acttagctta      60
gctagcgaaa gctccgcctg cgacttacca gaaactcaca gtcttgataa taggagaact    120
ttgatgttat tggctcagat gagtagaata tctccttctt cttgtttgat ggatagacat    180
gacttcggat ttccacaaga ggagtttgat ggtaatcaat ttcaaaaggc tccagctatt    240
tctgtattac atgagttgat tcagcaaatt ttcaatctgt ttactacaaa ggattcatct    300
gctgcatggg atgaggatct cttagataaa ttttgtactg aattgtatca acagcttaat    360
gatttggaag cttgtgtgat gcaggaggag agagtgggtg agactccatt gatgaatgct    420
gactccatac tggcagtgaa gaaatacttc agacgtatca cactttacct gacagaaaag    480
aaatactcac cttgtgcctg ggaggttgtc agagcgaaa tacgaagatg tttgtattat    540
ttttataagt ttactgcact attccgtaga aaagagcacc atcaccatca ccataaggac    600
gaactgtga                                                            609
```

<210> SEQ ID NO 2
<211> LENGTH: 609
<212> TYPE: DNA
<213> ORGANISM: Artificial
<220> FEATURE:
<223> OTHER INFORMATION: shuffled variant of human interferon

<400> SEQUENCE: 2

```
atgggaaaaa tggcttctct atttgccaca ttttagtgg ttttagtgtc acttagctta      60
gctagcgaaa gctccgcctg cgacttacca gaaactcaca gtcttgataa taggagaact    120
ttgatgttat tggctcagat gagtagaata tctccttctt cttgtttgat ggatagacat    180
gacttcggat ttccacaaga ggagtttgat ggtaatcaat ttcaaaaggc tccagctatt    240
tctgtattac atgagttgat tcagcaaatt ttcaatctgt ttactacaaa ggattcatct    300
gctgcatggg atgaggatct cttagataaa ttttgtactg aattgtatca acagcttaat    360
gatttggaag cttgtgtgat gcaggaggag agagtgggtg agactccatt gatgaatgct    420
gactccatac tggcagtgaa gaaatacttc agacgtatca cactttacct gacagaaaag    480
aaatactcac cttgtgcctg ggaggttgtc agagcggaaa tacgaagatg tttgtattat    540
ttttataagt ttactgcact attacgtaga aaagagcacc atcaccatca ccataaggac    600
gaactgtga                                                            609
```

<210> SEQ ID NO 3
<211> LENGTH: 606
<212> TYPE: DNA
<213> ORGANISM: Artificial
<220> FEATURE:
<223> OTHER INFORMATION: shuffled variant of human interferon

<400> SEQUENCE: 3

```
atgggaaaaa tggcttctct atttgccaca ttttagtgg ttttagtgtc acttagctta      60
```

```
gctagcgaaa gctccgcctg cgacttacca gaaactcaca gtcttgataa taggagaact    120
ttgatgttat tggctcagat gagtagaata tctccttctt cttgtttgat ggatagacat    180
gacttcggat ttccacaaga ggagtttgat ggtaatcaat ttcaaaaggc tccagctatt    240
tctgtattac atgagttgat tcagcaaatt ttcaatctgt ttactacaaa ggattcatct    300
gctgcatggg atgaggatct cttagataaa ttttgtactg aattgtatca acagcttaat    360
gatttggaag cttgtgtgat gcaggaggag agagtgggtg agactccatt gatgaatgct    420
gactccatac tggcagtgaa gaaatacttc agacgtatca cactttacct gacagaaaag    480
aaatactcac cttgtgcctg ggaggttgtc agagcggaaa tacgaagatg tttgtattat    540 tttataagt ttactgcact attccgtaga aaacaccatc accatcacca taaggacgaa    600
ctgtga                                                                606
```

<210> SEQ ID NO 4
<211> LENGTH: 202
<212> TYPE: PRT
<213> ORGANISM: Artificial
<220> FEATURE:
<223> OTHER INFORMATION: translation of SEQ ID NO: 1

<400> SEQUENCE: 4

```
Met Gly Lys Met Ala Ser Leu Phe Ala Thr Phe Leu Val Val Leu Val
1               5                   10                  15

Ser Leu Ser Leu Ala Ser Glu Ser Ser Ala Cys Asp Leu Pro Glu Thr
            20                  25                  30

His Ser Leu Asp Asn Arg Arg Thr Leu Met Leu Leu Ala Gln Met Ser
        35                  40                  45

Arg Ile Ser Pro Ser Ser Cys Leu Met Asp Arg His Asp Phe Gly Phe
    50                  55                  60

Pro Gln Glu Glu Phe Asp Gly Asn Gln Phe Gln Lys Ala Pro Ala Ile
65                  70                  75                  80

Ser Val Leu His Glu Leu Ile Gln Gln Ile Phe Asn Leu Phe Thr Thr
                85                  90                  95

Lys Asp Ser Ser Ala Ala Trp Asp Glu Asp Leu Leu Asp Lys Phe Cys
            100                 105                 110

Thr Glu Leu Tyr Gln Gln Leu Asn Asp Leu Glu Ala Cys Val Met Gln
        115                 120                 125

Glu Glu Arg Val Gly Glu Thr Pro Leu Met Asn Ala Asp Ser Ile Leu
    130                 135                 140

Ala Val Lys Lys Tyr Phe Arg Arg Ile Thr Leu Tyr Leu Thr Glu Lys
145                 150                 155                 160

Lys Tyr Ser Pro Cys Ala Trp Glu Val Val Arg Ala Glu Ile Arg Arg
                165                 170                 175

Cys Leu Tyr Tyr Phe Tyr Lys Phe Thr Ala Leu Phe Arg Arg Lys Glu
            180                 185                 190

His His His His His His Lys Asp Glu Leu
        195                 200
```

<210> SEQ ID NO 5
<211> LENGTH: 202
<212> TYPE: PRT
<213> ORGANISM: Artificial
<220> FEATURE:
<223> OTHER INFORMATION: translation of SEQ ID NO: 2

<400> SEQUENCE: 5

```
Met Gly Lys Met Ala Ser Leu Phe Ala Thr Phe Leu Val Val Leu Val
1               5                   10                  15

Ser Leu Ser Leu Ala Ser Glu Ser Ser Ala Cys Asp Leu Pro Glu Thr
            20                  25                  30

His Ser Leu Asp Asn Arg Arg Thr Leu Met Leu Leu Ala Gln Met Ser
        35                  40                  45

Arg Ile Ser Pro Ser Ser Cys Leu Met Asp Arg His Asp Phe Gly Phe
    50                  55                  60

Pro Gln Glu Glu Phe Asp Gly Asn Gln Phe Gln Lys Ala Pro Ala Ile
65                  70                  75                  80

Ser Val Leu His Glu Leu Ile Gln Gln Ile Phe Asn Leu Phe Thr Thr
                85                  90                  95

Lys Asp Ser Ser Ala Ala Trp Asp Glu Asp Leu Leu Asp Lys Phe Cys
            100                 105                 110

Thr Glu Leu Tyr Gln Gln Leu Asn Asp Leu Glu Ala Cys Val Met Gln
            115                 120                 125

Glu Glu Arg Val Gly Glu Thr Pro Leu Met Asn Ala Asp Ser Ile Leu
        130                 135                 140

Ala Val Lys Lys Tyr Phe Arg Arg Ile Thr Leu Tyr Leu Thr Glu Lys
145                 150                 155                 160

Lys Tyr Ser Pro Cys Ala Trp Glu Val Val Arg Ala Glu Ile Arg Arg
                165                 170                 175

Cys Leu Tyr Tyr Phe Tyr Lys Phe Thr Ala Leu Leu Arg Arg Lys Glu
            180                 185                 190

His His His His His His Lys Asp Glu Leu
        195                 200

<210> SEQ ID NO 6
<211> LENGTH: 201
<212> TYPE: PRT
<213> ORGANISM: Artificial
<220> FEATURE:
<223> OTHER INFORMATION: translation of SEQ ID NO: 3

<400> SEQUENCE: 6

Met Gly Lys Met Ala Ser Leu Phe Ala Thr Phe Leu Val Val Leu Val
1               5                   10                  15

Ser Leu Ser Leu Ala Ser Glu Ser Ser Ala Cys Asp Leu Pro Glu Thr
            20                  25                  30

His Ser Leu Asp Asn Arg Arg Thr Leu Met Leu Leu Ala Gln Met Ser
        35                  40                  45

Arg Ile Ser Pro Ser Ser Cys Leu Met Asp Arg His Asp Phe Gly Phe
    50                  55                  60

Pro Gln Glu Glu Phe Asp Gly Asn Gln Phe Gln Lys Ala Pro Ala Ile
65                  70                  75                  80

Ser Val Leu His Glu Leu Ile Gln Gln Ile Phe Asn Leu Phe Thr Thr
                85                  90                  95

Lys Asp Ser Ser Ala Ala Trp Asp Glu Asp Leu Leu Asp Lys Phe Cys
            100                 105                 110

Thr Glu Leu Tyr Gln Gln Leu Asn Asp Leu Glu Ala Cys Val Met Gln
            115                 120                 125

Glu Glu Arg Val Gly Glu Thr Pro Leu Met Asn Ala Asp Ser Ile Leu
        130                 135                 140

Ala Val Lys Lys Tyr Phe Arg Arg Ile Thr Leu Tyr Leu Thr Glu Lys
145                 150                 155                 160
```

```
Lys Tyr Ser Pro Cys Ala Trp Glu Val Val Arg Ala Glu Ile Arg Arg
            165                 170                 175

Cys Leu Tyr Tyr Phe Tyr Lys Phe Thr Ala Leu Phe Arg Arg Lys His
            180                 185                 190

His His His His His Lys Asp Glu Leu
            195                 200

<210> SEQ ID NO 7
<211> LENGTH: 192
<212> TYPE: PRT
<213> ORGANISM: Artificial
<220> FEATURE:
<223> OTHER INFORMATION: SEQ ID NO: 4 with terminal 6 His and KDEL
      removed

<400> SEQUENCE: 7

Met Gly Lys Met Ala Ser Leu Phe Ala Thr Phe Leu Val Val Leu Val
1               5                   10                  15

Ser Leu Ser Leu Ala Ser Glu Ser Ser Ala Cys Asp Leu Pro Glu Thr
            20                  25                  30

His Ser Leu Asp Asn Arg Arg Thr Leu Met Leu Leu Ala Gln Met Ser
            35                  40                  45

Arg Ile Ser Pro Ser Ser Cys Leu Met Asp Arg His Asp Phe Gly Phe
50                  55                  60

Pro Gln Glu Glu Phe Asp Gly Asn Gln Phe Gln Lys Ala Pro Ala Ile
65                  70                  75                  80

Ser Val Leu His Glu Leu Ile Gln Gln Ile Phe Asn Leu Phe Thr Thr
            85                  90                  95

Lys Asp Ser Ser Ala Ala Trp Asp Glu Asp Leu Leu Asp Lys Phe Cys
            100                 105                 110

Thr Glu Leu Tyr Gln Gln Leu Asn Asp Leu Glu Ala Cys Val Met Gln
            115                 120                 125

Glu Glu Arg Val Gly Glu Thr Pro Leu Met Asn Ala Asp Ser Ile Leu
            130                 135                 140

Ala Val Lys Lys Tyr Phe Arg Arg Ile Thr Leu Tyr Leu Thr Glu Lys
145                 150                 155                 160

Lys Tyr Ser Pro Cys Ala Trp Glu Val Val Arg Ala Glu Ile Arg Arg
            165                 170                 175

Cys Leu Tyr Tyr Phe Tyr Lys Phe Thr Ala Leu Phe Arg Arg Lys Glu
            180                 185                 190

<210> SEQ ID NO 8
<211> LENGTH: 192
<212> TYPE: PRT
<213> ORGANISM: Artificial
<220> FEATURE:
<223> OTHER INFORMATION: SEQ ID NO: 5 with terminal 6 His and KDEL
      removed

<400> SEQUENCE: 8

Met Gly Lys Met Ala Ser Leu Phe Ala Thr Phe Leu Val Val Leu Val
1               5                   10                  15

Ser Leu Ser Leu Ala Ser Glu Ser Ser Ala Cys Asp Leu Pro Glu Thr
            20                  25                  30

His Ser Leu Asp Asn Arg Arg Thr Leu Met Leu Leu Ala Gln Met Ser
            35                  40                  45

Arg Ile Ser Pro Ser Ser Cys Leu Met Asp Arg His Asp Phe Gly Phe
50                  55                  60
```

```
Pro Gln Glu Glu Phe Asp Gly Asn Gln Phe Gln Lys Ala Pro Ala Ile
 65                  70                  75                  80

Ser Val Leu His Glu Leu Ile Gln Gln Ile Phe Asn Leu Phe Thr Thr
                 85                  90                  95

Lys Asp Ser Ser Ala Ala Trp Asp Glu Asp Leu Leu Asp Lys Phe Cys
                100                 105                 110

Thr Glu Leu Tyr Gln Gln Leu Asn Asp Leu Glu Ala Cys Val Met Gln
            115                 120                 125

Glu Glu Arg Val Gly Glu Thr Pro Leu Met Asn Ala Asp Ser Ile Leu
        130                 135                 140

Ala Val Lys Lys Tyr Phe Arg Arg Ile Thr Leu Tyr Leu Thr Glu Lys
145                 150                 155                 160

Lys Tyr Ser Pro Cys Ala Trp Glu Val Val Arg Ala Glu Ile Arg Arg
                165                 170                 175

Cys Leu Tyr Tyr Phe Tyr Lys Phe Thr Ala Leu Leu Arg Arg Lys Glu
            180                 185                 190
```

<210> SEQ ID NO 9
<211> LENGTH: 191
<212> TYPE: PRT
<213> ORGANISM: Artificial
<220> FEATURE:
<223> OTHER INFORMATION: SEQ ID NO: 6 with terminal 6 His and KDEL
      removed

<400> SEQUENCE: 9

```
Met Gly Lys Met Ala Ser Leu Phe Ala Thr Phe Leu Val Val Leu Val
 1               5                  10                  15

Ser Leu Ser Leu Ala Ser Glu Ser Ala Cys Asp Leu Pro Glu Thr
                 20                  25                  30

His Ser Leu Asp Asn Arg Arg Thr Leu Met Leu Leu Ala Gln Met Ser
             35                  40                  45

Arg Ile Ser Pro Ser Ser Cys Leu Met Asp Arg His Asp Phe Gly Phe
        50                  55                  60

Pro Gln Glu Glu Phe Asp Gly Asn Gln Phe Gln Lys Ala Pro Ala Ile
 65                  70                  75                  80

Ser Val Leu His Glu Leu Ile Gln Gln Ile Phe Asn Leu Phe Thr Thr
                 85                  90                  95

Lys Asp Ser Ser Ala Ala Trp Asp Glu Asp Leu Leu Asp Lys Phe Cys
                100                 105                 110

Thr Glu Leu Tyr Gln Gln Leu Asn Asp Leu Glu Ala Cys Val Met Gln
            115                 120                 125

Glu Glu Arg Val Gly Glu Thr Pro Leu Met Asn Ala Asp Ser Ile Leu
        130                 135                 140

Ala Val Lys Lys Tyr Phe Arg Arg Ile Thr Leu Tyr Leu Thr Glu Lys
145                 150                 155                 160

Lys Tyr Ser Pro Cys Ala Trp Glu Val Val Arg Ala Glu Ile Arg Arg
                165                 170                 175

Cys Leu Tyr Tyr Phe Tyr Lys Phe Thr Ala Leu Phe Arg Arg Lys
            180                 185                 190
```

INTERFERON ALPHA AND INTERFERON KAPPA FUSION PROTEIN

CROSS REFERENCE TO RELATED APPLICATIONS

This application claims priority from U.S. Provisional Application No. 61/097,077, filed Sep. 15, 2008. The prior application is hereby incorporated by reference in its entirety.

STATEMENT REGARDING FEDERALLY SPONSORED RESEARCH OR DEVELOPMENT

This invention was made with Government support under contract (W81XWH-05-2-0009) awarded by U.S. Department of the Army. The Government has certain rights in the invention.

BACKGROUND OF THE INVENTION

This invention pertains to molecules with antiviral activity. More specifically, it deals with altered interferon molecules that are capable of interfering with the action of decoy receptors produced upon virus infection that alter the host immune response. It also deals with development of altered interferon molecules that are less sensitive to the effects of the decoy receptors.

The role of Type I interferons in antiviral defense have been well characterized (Immunity 2006 September; 25:373-81). Poxvirus has evolved specific mechanisms to interfere with these host defense responses. One of these mechanisms is to bind host interferon molecules and prevent them from functioning in their normal role in antiviral signaling (J. Virol. 2000 December; 74(23):11230-9). Although a number of poxvirus therapeutic strategies have been developed (J. Antimicrobial Chemotherapy 2004 May; 54:1-5), interference with this particular mechanism has not been thoroughly explored. This is partly due to the difficulty in producing large numbers of modified interferon molecules to screen for the desired properties.

BRIEF SUMMARY OF THE INVENTION

Poxviruses encode proteins that interfere with the innate immune response by binding and sequestering Type I interferon (IFN). To combat poxvirus infection, antagonists are developed that bind the soluble cytokine receptor but have no significant biological activity in the host, effectively blocking the virus-mediated suppressor of IFN function, thereby permitting the host's own cytokines to stimulate an antiviral response. Alternatively, IFN molecules can be developed that retain biological activity on their native receptors but fail to bind the viral cytokine binding protein, thereby circumventing this virus immune modulation mechanism.

BRIEF DESCRIPTION OF THE FIGURES

FIG. 2: Daudi cells were incubated in the presence of IFN alpha-2a alone, with B18R alone, or with both B18R and NB-001. The dramatic reduction of IFN activity after addition of B18R protein was almost completely reversed by NB-001.

FIG. 3: Sequences represent NB-001 (10445_C8, SEQ ID NO: 1) and two closely related shufflants (10442_H8, SEQ ID NO: 2 and 10453_H9, SEQ ID NO: 3). All are comprised of IFN alpha-1 with a small portion of IFN Kappa near their C-terminus. When this portion of IFN Kappa was inserted into other IFNs such as IFN alpha-2a, the resulting molecules had activities similar to NB-001.

FIG. 4: SEQ ID NOs: 4, 5 and 6 are the amino acid translation of SEQ ID NOs: 1, 2 and 3 respectively. SEQ ID NOs: 7, 8 and 9 comprise the amino acid sequences of SED ID NOs: 4, 5 and 6 respectively with the C-terminal six Histidines and endoplasmic reticulum retention signal removed to restore a more native-like C-terminus.

DETAILED DESCRIPTION OF THE INVENTION

Figure 1:
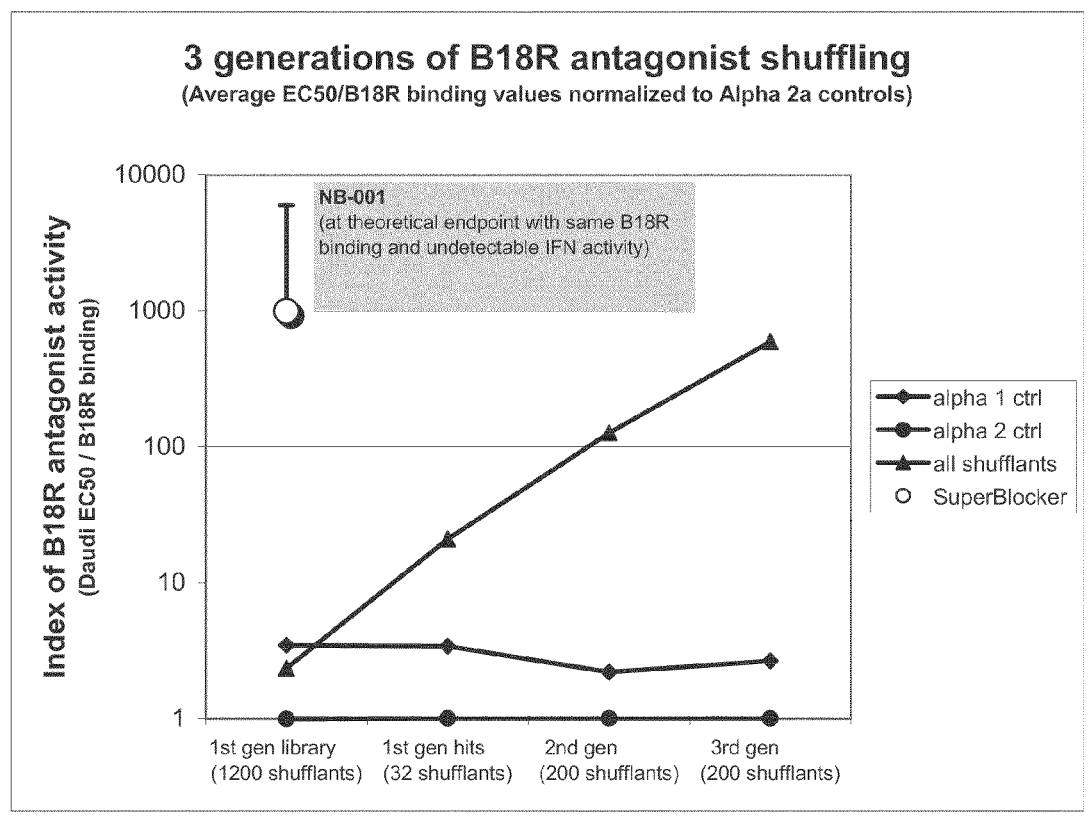
FIG. 1: Progressive increase in index of B18R antagonist activity over three generations of GRAMMR® shuffling and screening.

We produced libraries of gene shuffled human interferon proteins and screened them with a combination of cellular activity assays and biochemical binding assays to identify molecules with altered ratios in their biological activity relative to their binding to a poxvirus soluble cytokine receptor protein. Shuffled molecules with improved properties were identified and taken through additional rounds of shuffling and screening to evolve chimeric interferons with the ability to block the function of the soluble cytokine receptor. A region of particular interest that was highlighted by these studies is located near the C-terminal end of the interferon protein. This region, especially when derived from human interferon kappa, showed particularly desirable effects.

Libraries of shuffled IFN molecules were made in an effort to develop variants with enhanced antiviral activities. Typical antiviral screens employ pretreatment of cultured cells with the shuffled IFN samples followed by infection with target viruses engineered to express a reporter gene. The extent to which the virus-produced signal is altered by a given concentration of IFN relative to controls is a measurement of the relative antiviral potency of that IFN molecule. To simplify screening efforts, cell lines used for antiviral screening often do not contain a functional alpha-IFN gene locus. Because such cell lines lack the paracrine IFN cellular response, their use simplifies the measurement of antiviral potency of any given shuffled IFN candidate. Although this approach may be an efficient way to identify IFN variants with enhanced activities, especially against viruses that employ only intracellular mechanisms to down-regulate IFN signaling, it does not directly address some of the mechanisms that orthopoxviruses employ to inhibit the paracrine IFN response.

Many poxviruses encode immunomodulatory proteins that interfere with the normal host immune response. Orthopoxviruses produce a decoy cytokine receptor that binds to Type I IFNs with broad subtype and species specificity. In the case of variola and vaccinia viruses, this protein is B18R. The monkeypox homolog is the B16R protein. It is believed that after this virally-encoded soluble receptor protein is produced and secreted early in the virus life cycle, it adheres to neighboring cells and binds incoming Type I interferon molecules, thereby interfering with activation of an effective antiviral response in those cells.

Although these virally encoded cytokine binding proteins have been shown to have very broad species and subtype specificity for Type I IFNs, some IFNs are bound more efficiently than others. In addition, different Type I IFNs also exhibit distinct biological activities, presumably through differences in their interaction with the cellular Type I IFN receptor. While these separate protein binding activities of IFNs may be related, they do not necessarily share perfect correspondence. Hence, the possibility exists that B18R binding and cellular receptor activation can be independently altered through changes in the IFN molecule to create variant IFNs that exhibit differential binding to the viral decoy protein and the host receptor proteins. If so, variant IFNs may be produced that show normal binding to one, but reduced interaction with the other.

To begin the search for variants with this behavior, libraries of chimeric Type I human interferon genes were generated using GRAMMR® gene shuffling (see, for example, U.S. Pat. No. 7,056,740). The corresponding chimeric proteins were then produced in plants using a virus-based transient plant expression system followed by extraction and immobilized metal affinity chromatography to purify the proteins. Each of the resulting proteins was then assayed with both a biological assay and a biochemical assay to identify shufflants with increased differentials in their relative binding values. Iterative rounds of shuffling and screening were then performed using the best variants from one round as parents for the next round.

The goal of this directed evolution effort was to obtain maximal differentiation between B18R binding and activation of the cellar IFN receptor. This differentiation could be accomplished by either 1), diminishing cellular receptor activation while maintaining B18R binding, or 2), selecting the converse set of properties in which cellular activation is maintained but B18R binding is reduced.

In the case of the former, molecules could be developed that still bind B18R but have decreased ability to trigger the cellular IFN response. Such molecules might be useful for administration pre- or post-exposure to smallpox to neutralize the B18R-mediated IFN suppression mechanism. Because such decoy receptor antagonists would lack biological activity in the host, it may be possible to administer to patients in much higher doses than could be used with standard functional interferons. Moreover, the broad subtype and species specificity of poxvirus Type I IFN binding proteins suggests that an antagonist of this nature could be effective against a broad range of poxvirus species, strains, and mutants. This potentially broad activity against poxviruses could also be effective in combination with other antiviral therapies including interferons and virus neutralizing antibodies as well as small molecule antivirals such as ST246 and cidofivir, especially in light of the demonstrated ability of poxviruses to develop drug resistance against the small molecule therapeutic compounds.

In the case of molecules that are evolved to circumvent the virus decoy receptors while retaining normal levels of cellular IFN receptor activation activity, they would remain capable of stimulating a successful antiviral response against orthopoxviruses despite the presence of B18R. Moreover, if one were to start with an already broadly active interferon, making it resistant to poxvirus B18R would be expected to broaden its activity even further without compromising its utility for treatment of other virus infections.

Experiments were performed to identify and further develop IFN molecules with the properties described above. These experiments included both a biological assay and a biochemical assay. Consistent with what has previously been reported in the literature, we found that recombinant vaccinia B18R protein can neutralize IFN alpha-2a. When the two were mixed prior to incubation with Daudi cells, no antiproliferative effects of the IFN were observed in the presence of equivalent amounts (on a molar basis) of B18R, indicating that B18R neutralized the IFN alpha-2a.

In order to characterize the binding of libraries of shuffled IFNs to B18R, a competitive ELISA-based assay was developed that provided very sensitive detection of the interaction between the shuffled IFNs relative to a biotin labeled IFN alpha-2a. Because of the strong interaction between B18R and IFN, even moderate changes in B18R binding of IFNs could be registered. This assay served as the basis for a directed evolution effort to develop shuffled IFN antagonists as well as IFNs with reduced B18R interaction.

Over three generations of recursive shuffling and screening, successive improvement in the index of B18R antagonism (Daudi EC50 value/B18R binding value) was obtained (FIG. 1). In addition to evolving a marked increase in the index of B18R antagonism, one class of gene shuffled IFN molecule was discovered in the first-generation libraries that had met the theoretical endpoint of the assay (wild-type B18R binding and undetectable cellular bioactivity). Although these molecules were obtained after the first round of shuffling, their sequence configuration would have been difficult to obtain with gene shuffling methods other than GRAMMR®.

Figure 2:
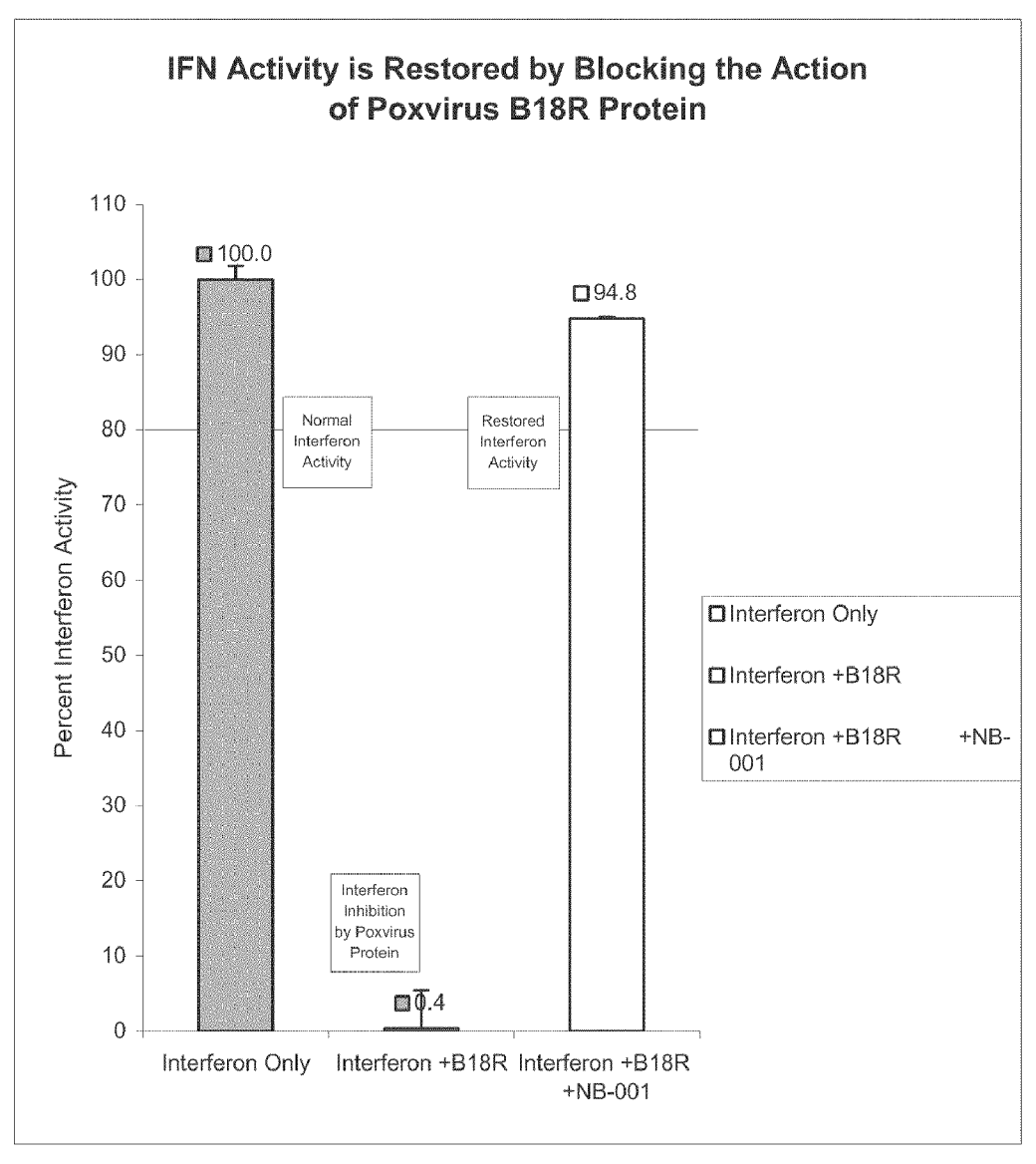

In cellular assays, this Superblocker (NB-001) is able to reverse the B18R protein's IFN inhibitory activity (FIG. 2) when pre-incubated in modest excess with B18R protein. Alone, NB-001 showed no endogenous IFN activity in Daudi cell assays. The fact that IFN can be shielded from the immunosuppressive effects of poxvirus B18R in culture suggests that the NB-001 may be useful to bolster the innate immune system against poxvirus attack in vivo.

Other viruses with large genomes, such as herpesviruses also encode immunomodulatory molecules including cytokine binding proteins, chemokine binding proteins, and complement inhibitory proteins. Development of molecules that either bind and antagonize or circumvent these viral counterdefenses can be accomplished using the same lines of logic described here for modified IFNs that antagonize or circumvent vaccinia B18R.

Beyond the development of antiviral agents that are designed to either block or circumvent virus-encoded soluble cytokine receptors, it may be possible to develop molecules that can interact with host-encoded proteins that modulate other cytokine, chemokine, and other signaling molecule activities and that may contribute to the development and maintenance of certain cancers. It has been shown that through a virally-encoded transcription factor, Epstein-Barr virus (EBV) specifically activates transcription of the host Decoy Receptor 3 (DcR3) protein, a member of the tumor necrosis factor receptor superfamily and a secreted protein that is believed to contribute to tumor cell survival by inhibiting apoptosis and by interfering with immune surveillance (J Virol. 2007 May; 81(9):4837-47). Because of these properties, DcR3 may play a role in the development of EBV-linked cancer. In addition, several forms of cancer have been found to be associated with elevated levels of DCR3, which may contribute to tumor survival through its immune modulating properties. Antagonism of DCR3 and reduction of its impact on the immune system may be made possible through the development of antagonist molecules that bind DCR3 but lack appreciable activity on their corresponding, and also very similar, cell-surface receptors.

What is claimed is:

1. An isolated polynucleotide comprising a nucleic acid sequence selected from the group consisting of SEQ ID NO: 1, SEQ ID NO: 2, and SEQ ID NO: 3.

2. An isolated protein comprising an amino acid sequence selected from the group consisting of SEQ ID NO: 4, SEQ ID NO: 5, and SEQ ID NO: 6.

* * * * *